United States Patent [19] [11] Patent Number: 4,581,456
Barnett [45] Date of Patent: Apr. 8, 1986

[54] PROCESSES FOR PREPARING PICENADOL PRECURSORS AND NOVEL INTERMEDIATES THEREOF

[75] Inventor: Charles J. Barnett, Indianapolis, Ind.

[73] Assignee: Eli Lilly and Company, Indianapolis, Ind.

[21] Appl. No.: 534,468

[22] Filed: Sep. 21, 1983

[51] Int. Cl.$^4$ .................... C07D 211/22; C07D 211/02
[52] U.S. Cl. ..................................... 546/185; 546/236; 546/194; 546/281; 546/334; 544/124; 544/360
[58] Field of Search ................................ 546/236, 185

[56] References Cited

U.S. PATENT DOCUMENTS

| | | | |
|---|---|---|---|
| 2,845,431 | 7/1958 | Lutz et al. | 546/185 |
| 3,177,258 | 4/1965 | Rylander et al. | 546/185 |
| 3,946,086 | 3/1976 | Gershanov et al. | 568/744 |
| 4,081,450 | 3/1978 | Zimmerman | 260/293.64 |

OTHER PUBLICATIONS

Lieberman et al., in *J. Org. Chem.* 14, 1001–1012 (1949).
Evans et al., in *J. Am. Chem. Soc.* 102, 5955–5956 (1980).
Marchand in *Chem. Ber.* 95, 577–578 (1962).
Schreiber et al., in *Angew, Chem. Internat. Edit.*, vol. 10, No. 5, 330 (1971).
Bryson et al., in *J. Org. Chem.* 45, 524–525 (1980).
Herbert O. House, "Modern Synthetic Reactions", 2nd edition (1972), pp. 654–655.
K. Blaha et al., Advances in Heterocyclic Chemistry, vol. 6 (1966), p. 219.
Martinez et al., Tetrahedron, vol. 34 (1978), pp. 3027–3036.
Beeken et al., J. Org. Chem., vol. 45 (1980), pp. 1336–1338.

*Primary Examiner*—Nora S. Milestone
*Attorney, Agent, or Firm*—Bruce J Barclay; Arthur R. Whale

[57] ABSTRACT

The present invention relates to processes for preparing precursors of picenadol, ($\pm$)3-(1,3$\alpha$-dimethyl-4$\alpha$-propyl-4$\beta$-piperidinyl)phenol, hydrochloride, a known analgesic. Certain of the compounds prepared by the present process are novel as well.

7 Claims, No Drawings

PROCESSES FOR PREPARING PICENADOL PRECURSORS AND NOVEL INTERMEDIATES THEREOF

SUMMARY OF THE INVENTION

The present invention relates to a new and improved process for preparing a 1,4-dialkyl-3-methyl-4-(3-substituted phenyl)piperidine of the formula

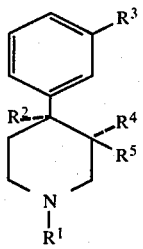

wherein $R^1$ and $R^2$ are independently $C_1$–$C_4$ alkyl, $R^3$ is $C_1$–$C_3$ alkoxy, and one of $R^4$ and $R^5$ is methyl and the other is hydrogen, comprising reacting a 1,4-dialkyl-4-(3-substituted phenyl)-tetrahydropyridine of the formula

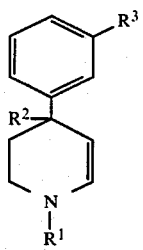

with formaldehyde and $NHR^6R^7$, wherein $R^6$ and $R^7$ are independently $C_1$–$C_3$ alkyl or, when taken together with the nitrogen atom to which they are attached, form piperidine, piperazine, N-methylpiperazine, morpholine or pyrrolidine, at a pH from about 1.0 to about 5.0, and in the presence of an acid which provides a non-nucleophilic anion, to prepare a 1,4-dialkyl-4-(3-substituted phenyl)-3-tetrahydropyridinemethanamine of the formula

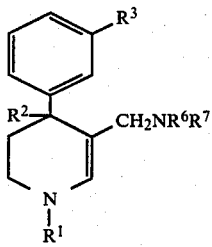

and reducing that product by hydrogenation over a palladium catalyst in a basic reaction medium.

The present invention also relates to a process for preparing a 1,4-dialkyl-4-(3-substituted phenyl)-3-tetrahydropyridinemethanamine from a 1,4-dialkyl-4-(3-substituted phenyl)-tetrahydropyridine as described above.

Provided as another embodiment of the present invention is a process for isolating a $(\pm)$-3-(1,4α-dialkyl-3α-methyl-4β-piperidinyl)phenol of the formula

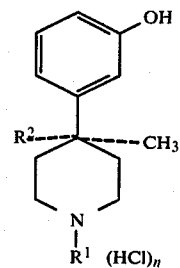

wherein $R^1$ and $R^2$ are independently $C_1$–$C_4$ alkyl and n is 0 or 1, from a diastereomeric mixture of the formula

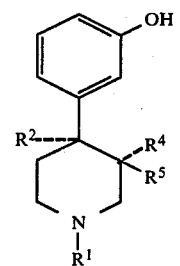

wherein $R^1$ and $R^2$ are independently $C_1$–$C_4$ alkyl and one of $R^4$ and $R^5$ is methyl and the other is hydrogen, comprising one of the following steps:

a. when n is one, dissolving the diastereomeric mixture in aqueous hydrochloric acid at approximately 50° C. to 100° C., cooling the solution and collecting the precipitated 3α-methyl dihydrate salt by filtration; or b. when n is 0, recrystallizing the diastereomeric mixture from acetonitrile:ethyl acetate (5:1) and collecting the less soluble 3α-methyl derivative by filtration.

Provided as yet a further embodiment of the present invention is a novel compound of the formula

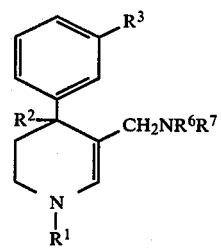

wherein:
$R^1$ and $R^2$ are independently $C_1$–$C_4$ alkyl;
$R^3$ is $C_1$–$C_3$ alkoxy; and
$R^6$ and $R^7$ are independently $C_1$–$C_3$ alkyl or, when taken together with the nitrogen atom to which they are attached, form piperidine, piperazine, N-methylpiperazine, morpholine or pyrrolidine.

DETAILED DESCRIPTION OF THE INVENTION

In the above formulas, the term $C_1$–$C_4$ alkyl represents a straight or branched alkyl chain having from one to four carbon atoms. Typical $C_1$–$C_4$ alkyl groups include methyl, ethyl, n-propyl, isopropyl, n-butyl, isobutyl, sec.-butyl and t-butyl.

$C_1$–$C_3$ Alkoxy represents a straight or branched alkoxy chain having from one to three carbon atoms. Typical $C_1$–$C_3$ alkoxy groups are methoxy, ethoxy, n-propoxy and isopropoxy.

While the entire scope of process variables taught herein are believed operable, the present processes and compounds do have preferred aspects. Preferred compounds have the above formulas wherein $R^1$ is methyl and $R^2$ is n-propyl. Especially preferred compounds are wherein $R^3$ is methoxy and $R^6$ and $R^7$ are both methyl. Other preferred aspects of the present invention will be noted hereinafter.

It will be noted in the above formulas that the piperidines occur as stereochemical isomers by virtue of the substituents at the 3 and 4-positions. In particular, the methyl group at the 3-position can be situated either in an $\alpha$ or $\beta$ position relative to the alkyl group at the 4-position. The $\alpha$-stereochemistry exists where the methyl group at the 3-position of the piperidine ring is trans to the substituted phenyl group at the 4-position. It will be noted that a preferred aspect of the present processes is to maximize the desired $\alpha$-stereo-chemistry.

The novel process of the present invention may be represented by the following reaction scheme:

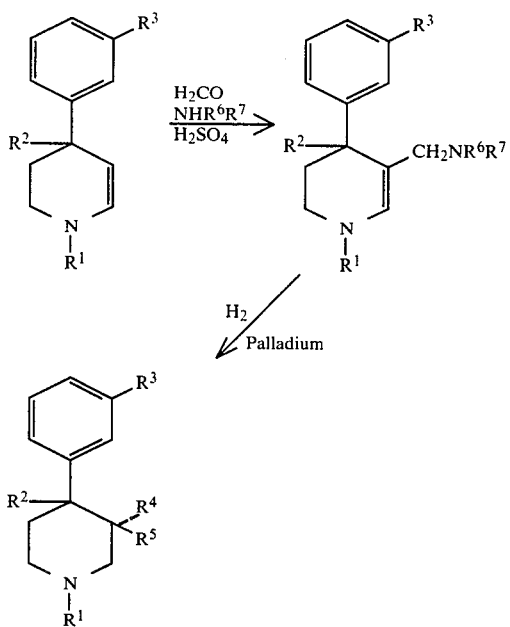

The first step in the process of the present invention involves the application of the Mannich reaction of aminomethylation to non-conjugated, endocyclic enamines. This reaction is carried out by combining from about 1.2 to 2.0 equivalents of aqueous formaldehyde and about 1.3 to 2.0 equivalents of the secondary amine $NHR^6R^7$ in a suitable solvent. While water is the preferred solvent, other non-nucleophilic solvents such as acetone and acetonitrile may also be employed in this reaction. The pH of this solution is adjusted to approximately 3.0–4.0 with an acid which provides a non-nucleophilic anion. Examples of such acids include sulfuric acid, the sulfonic acids such as methanesulfonic acid and para-toluenesulfonic acid, phosphoric acid, and tetrafluoroboric acid. The preferred acid is sulfuric acid. To this solution is added one equivalent of 1,4-dialkyl-4-(3-substituted phenyl)tetrahydropyridine, typically dissolved in aqueous sulfuric acid, and the pH of the solution readjusted to from 3.0–3.5 with the non-nucleophilic acid or a secondary amine as defined above. While maintenance of this pH during the reaction is preferred for optimum results, this reaction may be conducted at a pH in the range of from about 1.0 to 5.0. The reaction is substantially complete after about 1 to 4 hours, more typically about 2 hours, when conducted at a temperature in the range of from about 50° C. to about 80° C., more preferably at about 70° C. The reaction is next cooled to approximately 30° C. and added to a sodium hydroxide solution. This solution is extracted with an organic water immiscible solvent, such as hexane or ethyl acetate, and the organic phase, following thorough washing with water to remove any residual formaldehyde, is evaporated to dryness under reduced pressure.

The second step of the process of the present invention involves the catalytic hydrogenation of the 1,4-dialkyl-4-(3-substituted phenyl)-3-tetrahydropyridinemethanamine prepared above to the corresponding 1,4-dialkyl-3-methyl-4-(3-substituted phenyl)-piperidine. This reaction actually occurs in two steps. The first step is the hydrogenolysis reaction wherein the exo C-N bond is reductively cleaved thereby generating the 3-methyltetrahydropyridine. In the second step, the 2,3-double bond in the tetrahydropyridine ring is reduced thereby affording the desired piperidine ring.

Reduction of the enamine double bond introduces the crucial relative stereochemistry at the 3 and 4 carbon atoms of the piperidine ring. The present reduction does not occur with complete stereoselectivity. Experimental studies have shown several conditions to be important so as to optimize the quantity of compound having the desired $\alpha$-methyl substituent at the 3-position of the piperidine ring.

The catalysts employed in the process of the present invention are chosen from among the various palladium catalysts. Such palladium catalysts include palladium on carbon, palladium on calcium carbonate and palladium chloride on calcium carbonate.

The catalytic hydrogenation step of the process of the present invention is preferably conducted in a basic reaction medium as an acidic reaction medium is detrimental to a proper stereochemical outcome. Suitable bases for use in this reaction include the amine bases, especially triethylamine. The alkali metal hydroxides may also be employed, for example sodium hydroxide and potassium hydroxide. Further, employing catalysts having a basic substrate also contribute to the presence of a basic reaction medium. Preferred catalysts of this type are palladium on calcium carbonate and palladium chloride on calcium carbonate. When triethylamine is used as the base for the hydrogenolysis, no other solvent is needed. However, other solvents may be used with triethylamine in this step of the process. Suitable solvents include the alcohols, such as methanol or ethanol, as well as ethyl acetate, tetrahydrofuran, toluene, hexane, and the like. However, when more than an equivolume of ethanol is combined with triethylamine stereoselectivity of the reaction decreases, that is, more 3$\beta$-methylpiperidine is synthesized.

Proper stereochemical outcome has been shown to be dependent on the quantity of catalyst employed. The quantity of catalyst required to produce the desired stereochemical result is dependent upon the purity of the starting materials in regard to the presence or absence of various catalyst poisons. Typically, the more impure the starting material, the more catalyst is required to obtain the desired α-stereochemistry. Five to ten percent palladium or carbon at 25% to 50% weight of gross catalyst to weight of substrate reduced is preferred.

The purity of the 1,4-dialkyl-4-(3-substituted phenyl)-3-tetrahydropyridinemethanamine is also important to optimize the desired α-stereochemistry of the reaction. This compound is preferably purified with water washing as described hereinafter so as to remove catalyst poisons which have a tendency to slow hydrogen uptake.

The hydrogen pressure in the reaction vessel is not critical but may be in the range of from about 5 to 200 psi.

Concentration of the starting material by volume should preferably be around 20 ml. of liquid per gram of starting material, although an increased or decreased concentration of the starting material could also be employed.

Under the conditions as specified herein, the length of time for the catalytic hydrogenation is not critical because of the inability for over-reduction of the molecule. While the reaction may continue for up to 24 hours or longer, it is not necessary to continue the reduction conditions after the uptake of the theoretical two moles of hydrogen.

The product is isolated by filtering the reaction mixture through infusorial earth and evaporating the filtrate to dryness under reduced pressure. Further purification of the product thus isolated is not necessary and preferably the diastereomeric mixture is carried directly on to the following reaction.

Separation of the diastereomers obtained from the catalytic hydrogenation preferably does not occur until after the demethylation of the alkoxy compound prepared above to the corresponding phenol. This reaction is generally carried out by reacting the diastereomers in a 48% aqueous hydrobromic acid solution. This reaction is substantially complete after about 30 minutes to 24 hours when conducted at a temperature between 50° C. to about 150° C., more preferably at the reflux temperature of the reaction mixture. The mixture is then worked up by cooling the solution, followed by neutralization with base to an approximate pH of 8. This aqueous solution is extracted with a water immiscible organic solvent. The residue following evaporation of the organic phase is then preferably used directly in the following isomer separation step.

Another aspect of the present invention relates to a process for isolating a (±)-3-(1,4α-dialkyl-3α-methyl-4β-piperidinyl)phenol or its hydrochloric acid salt from the diastereomeric mixture prepared above.

The 3α-methylpiperidine hydrochloride salt is much less water soluble than the corresponding β derivative. Therefore, the two isomers may be separated as follows. The crude mixture of diastereomers is heated to a temperature of about 80° C. in approximately one equivalent of hydrochloric acid and the solution filtered hot. Upon gradual cooling, the desired crystalline α-isomer dihydrate hydrochloride salt precipitates out of solution and is collected by filtration. The 3α-methyl dihydrate salt thus obtained can be further purified by recrystallization from ethanol if desired to provide the anhydrate form of the hydrochloric acid salt.

Isomer separation may alternatively be effected by selective crystallization of the 3α-methylpiperidine free base from the solvent mixture acetonitrile:ethyl acetate (5:1). This process involves dissolving the crude diastereomeric mixture in the solvent system, typically by the moderate application of heat, allowing the solution to cool, and collecting the precipitated 3α-methylpiperidine free base by filtration.

The 1,4-dialkyl-4-(3-substituted phenyl)tetrahydropyridine derivatives used as starting materials to the process of the present invention are typically prepared as follows. A 3-substituted bromobenzene derivative is converted to the 3-substituted phenyllithium analog by reaction with an alkyllithium reagent. The 3-substituted phenyllithium derivative is reacted with a 1-alkyl-4-piperidone to provide the corresponding 1-alkyl-4-(3-substituted phenyl)piperidinol derivative. The piperidinol thus prepared is dehydrated with acid to provide the corresponding 1-alkyl-4-(3-substituted phenyl)tetrahydropyridine derivative which readily undergoes a metalloenamine alkylation to provide the appropriate 1,4-dialkyl-4-(3-substituted phenyl)tetrahydropyridine derivative. This reaction sequence will be readily understood by the following scheme:

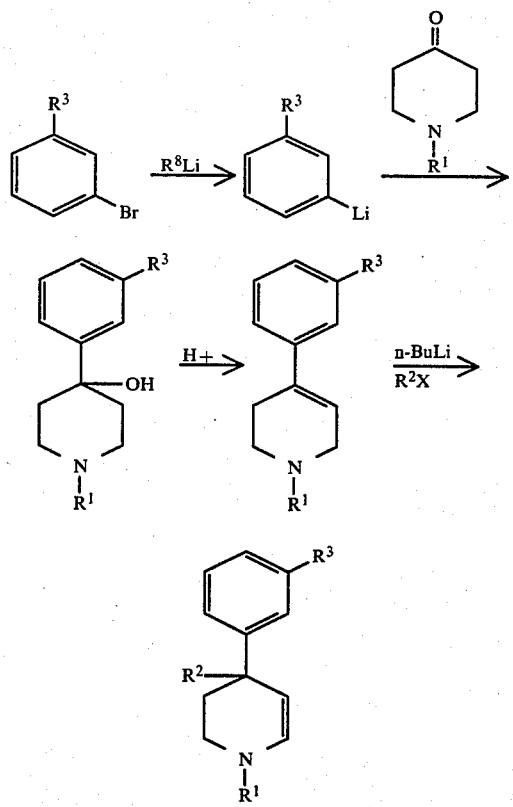

wherein $R^1$, $R^2$ and $R^3$ are as defined above, $R^8$ is $C_1$–$C_6$ alkyl and X is halogen.

The first step of the above-described process involves the formation of the 3-substituted phenyllithium reagent by reacting 3-substituted bromobenzene with an alkyllithium reagent. This reaction is typically performed under inert conditions and in the presence of a suitable non-reactive solvent such as dry diethyl ether or preferably dry tetrahydrofuran. Preferred alkyllithium reagents used in this process are n-butyllithium and especially sec.-butyllithium. Generally, approximately an equimolar to slight excess of alkyllithium reagent is added to the reaction mixture. The reaction is conducted at a temperature between −20° C. and −100° C. more preferably from −50° C. to −55° C. Once the 3-substituted phenyllithium reagent has formed, approximately an equimolar quantity of a 1-alkyl-4-piperidone is added to the mixture while maintaining the temperature between −20° C. and −100° C. The reaction is typically complete after about 1 to 24 hours. At this point, the reaction mixture is allowed to gradually warm to room temperature. The product is isolated by the addition of a saturated sodium chloride solution to the reaction mixture in order to quench any residual lithium reagent. The organic layer is separated and further purified if desired to provide the appropriate 1-alkyl-4-(3-substituted phenyl)-piperidinol derivative.

The dehydration of the 4-phenylpiperidinols prepared above is accomplished with a strong acid according to well known procedures. While dehydration occurs in various amounts with any one of several strong acids such as hydrochloric acid, hydrobromic acid, and the like, dehydration is preferably conducted with phosphoric acid, or especially p-toluenesulfonic acid and toluene or benzene. This reaction is typically conducted under reflux conditions, more generally from about 50° C. to about 150° C. The product thus formed is generally isolated by basifying an acidic aqueous solution of the salt form of the product and extracting the aqueous solution with any one of several water immiscible solvents. The resulting residue following evaporation may then be further purified if desired.

The 1,4-dialkyl-4-(3-substituted phenyl)tetrahydropyridine derivatives used as starting materials for the process of the present invention are prepared by a metalloenamine alkylation. This reaction is preferably conducted with n-butyllithium in tetrahydrofuran under an inert atmosphere, such as nitrogen or argon. Generally, a slight excess of n-butyllithium is added to a stirring solution of the 1-alkyl-4-(3-substituted phenyl)-tetrahydropyridine in THF cooled to a temperature in the range of from about −50° C. to about 0° C., more preferably from about −20° C. to about −10° C. This mixture is stirred for approximately 10 to 30 minutes followed by the addition of approximately from 1.0 to 1.5 equivalents of a $C_1$–$C_4$ alkyl halide to the solution while maintaining the temperature of the reaction mixture below 0° C. After about 5 to 60 minutes, water is added to the reaction mixture and the organic phase is collected. The product may be purified according to standard procedures, but it is desirable to purify the crude product by either distilling it under vacuum or slurrying it in a mixture of hexane:ethyl acetate (65:35) and silica gel for about 2 hours. According to the latter procedure, the product is then isolated by filtration and evaporating the filtrate under reduced pressure.

The following synthetic process illustrates the preparation of picenadol from commercially available starting materials and illustrates specific aspects of the present invention. All of the compounds prepared by the following processes were verified by nuclear magnetic resonance (NMR). For the NMR data provided herein, only the clearly assignable peaks have been listed.

PREPARATION OF 4-(3-METHOXYPHENYL)-1-METHYL4-PIPERIDINOL

A suitable dry reaction vessel having a mechanical stirrer, low temperature thermometer and addition funnel was charged with 250 g (1.34 mol) of m-bromoanisole (Aldrich Chemical Company, Milwaukee, Wis.) in 675 ml of dry tetrahydrofuran and the solution was cooled under nitrogen to −50° C. to −55° C. in a dry ice/acetone bath. A solution of 1357 ml. of sec.-butyllithium in cyclohexane (1.71 mol) was added dropwise to the reaction mixture at such a rate so that the temperature did not rise above −50° C. The resulting white suspension was stirred at −50° C. for 1 hour followed by the addition of 174.2 g (1.54 mol) of 1-methyl-4-piperidone (Aldrich Chemical Company) in 440 ml of dry tetrahydrofuran so as to maintain the reaction temperature below −40° C. When the addition was complete the temperature was allowed to rise to approximately −20° C. over approximately 1½ hours and then to room temperature over a 1 hour period. Residual sec.-butyllithium was quenched by the addition of 350 ml of saturated sodium chloride solution followed by the addition of 525 ml of water. The aqueous phase was separated and extracted twice with 350 ml portions of methylene chloride. The combined organic extracts were extracted in two portions, each with 1250 ml of 1N hydrochloric acid. The separated aqueous extracts were made basic (pH=10) with 28 percent ammonium hydroxide and extracted 3 times with 350 ml portions of methylene chloride. The organic phase was dried over anhydrous sodium sulfate and the solvent was evaporated in vacuo. The residue was slurried in 1000 ml of hot hexane and the slurry was cooled and filtered. The isolated crystalline product was dried in a vacuum oven to provide 225.6 g of 98% pure product.

Yield 74.4%. mp=111°–113° C.

NMR: (CDCl$_3$), δ2.30 (3H,S), 2.40(1H,S), 3.78 (3H,S), 6.8–7.3 (4H,m,aryl).

PREPARATION OF 1,2,3,6-TETRAHYDRO-4-(3-METHOXYPHENYL)-1-METHYLPYRIDINE

To 4.075 liters of 85% phosphoric acid at 60° C. in a 22 liter flask equipped with a condenser, thermometer, and stirrer was added portionwise 1.015 kg (4.35 mol) of 4-(3-methoxyphenyl)-1-methyl-4-piperidinol via a powder funnel. The reaction mixture was stirred for 3 hours at a temperature between 70° C. and 80° C. whereupon 4 liters of water was added and the temperature of the reaction mixture adjusted to approximately 50° C. The mixture was neutralized to pH 8.5 by the addition of 8.5 liters of 28% ammonium hydroxide while maintaining the temperature of the reaction mixture above 50° C. The resulting aqueous solution was extracted at 60° C. with 1.25 liters of hexane three times. The organic extracts were combined and washed twice with 1 liter of water, once with 0.5 liters of saturated sodium chloride solution and dried over 250 g of anhydrous sodium sulfate. Evaporation of the volatiles under reduced pressure provided 862.5 g of 97.9% pure 1,2,3,6-tetrahydro-4-(3-methoxyphenyl)-1-methylpyridine.

Yield 97.7%. mp (hydrobromide salt)=139.5°–141° C.

NMR:(CDCl$_3$)δ2.40 (3H,s), 2.62 (4H,m), 3.10 (2H,m), 3.80 (3H,s), 6.05 (1H,m), 6.7–7.3 (4H,m).

PREPARATION OF 1,2,3,4-TETRAHYDRO-4-(3-METHOXYPHENYL)-1-METHYL-4-PROPYLPYRIDINE

A solution of 900 g (4.43 mol) of 1,2,3,6-tetrahydro-4-(3-methoxyphenyl)-1-methylpyridine dissolved in 10.8 liters of dry THF was added to a dry, nitrogen purged 22 liter reaction flask equipped with a stirrer, low temperature thermometer, and addition funnel. The temperature of the reaction mixture was lowered to approximately −10° C. whereupon 3.04 liters of 1.6 molar n-butyllithium in hexane was added at a rate so as to maintain the temperature below −5° C. The resulting deep red solution was stirred for 15 minutes at −5° C. and 572 g (4.65 mol) of n-propylbromide in 2.4 liters of dry tetrahydrofuran were added at such a rate so that the temperature remained below −5° C. The reaction mixture was stirred for 10 minutes at −5° C. and then carefully quenched by the addition of 1.5 liters of water to destroy any excess n-butyllithium. The organic phase was separated, washed with 1.5 liters of water, 1.5 liters of saturated sodium chloride solution and dried over 500 g of anhydrous sodium sulfate. Evaporation of the solvent gave 1126 g of crude 1,2,3,4-tetrahydro-4-(3-methoxyphenyl)-1-methyl-4-propylpyridine (75% pure).

78% yield. bp=113° C./0.2 torr.

NMR: (CDCl$_3$)δ0.80 (3H,t), 2.57 (3H,s), 3.80 (3H,s), 4.58

(1H,d,A of AX, J=8), 5.95 (1H,d,X of AX, J=8), 6.8–7.3 (4H, m, aryl).

The following is an example of the silica gel purification technique. 1,2,3,4-Tetrahydro-4-(3-methoxyphenyl)-1-methyl-4-propylpyridine was purified according to the following procedure. To a solution of 65 g of crude 1,2,3,4-tetrahydro-4-(3-methoxy-phenyl)-1-methyl-4-propylpyridine in 680 ml of hexane: ethyl acetate (65:35) was added 65 g of silica gel to provide a slurry which was stirred at room temperature for 2 hours. The slurry was filtered and washed with 700 ml of hexane:ethyl acetate (65:35). Evaporation of the solvent gave 50.6 g of purified 1,2,3,4-tetrahydro-4-(3-methoxyphenyl)-1-methyl-4-propylpyridine. Yield 78%.

PREPARATION OF 1,4,5,6-TETRAHYDRO-4-(3-METHOXYPHENYL)-N,N,1-TRIMETHYL-4-PROPYL-3-PYRIDINEMETHANAMINE

To a solution of 10 g (0.123 mol) of 37% aqueous formaldehyde and 15 g (0.133 mol) of 40% aqueous dimethylamine in 100 ml of water was added enough concentrated sulfuric acid so as to adjust the pH of the reaction mixture to 3–4. A solution of 25 g (0.0867 mol) of 1,2,3,4-tetrahydro-4-(3-methoxyphenyl)-1-methyl-4-propylpyridine sulfate in approximately 40 ml of water was added and the pH adjusted to 3–3.5, if necessary, by the addition of sulfuric acid or 40% aqueous dimethylamine. The 1,2,3,4-tetrahydro-4-(3-methoxyphenyl)-1-methyl-4-propylpyridine sulfate solution was prepared by the extraction of 25 g of 1,2,3,4-tetrahydro-4-(3-methoxyphenyl)-1-methyl-4-propylpyridine in 50 ml of hexane with a total of about 40 ml of 2.5N sulfuric acid. The mixture was stirred at approximately 65°–70° C. for 2 hours while maintaining the pH of the reaction mixture between 3–3.5. The solution was cooled to 30° C. and added to 100 ml of 25% sodium hydroxide. The resulting suspension was extracted twice with 50 ml portions of hexane. The organic extracts were combined and washed five times with 50 ml portions of water, one time with a 50 ml portion of saturated sodium chloride and dried over 5 g of anhydrous sodium sulfate. Evaporation of the solvent under reduced pressure afforded 28.4 g of crude 1,4,5,6-tetrahydro-4-(3-methoxyphenyl)-N,N,1-trimethyl-4-propyl-3-pyridinemethanamine as an oil. Purity 85% by NMR. Yield 92.3%.

m/e Theory calculated for C$_{19}$H$_{30}$N$_2$O: 302.2376; Found 302.2394.

NMR: (CDCl$_3$)δ0.92 (3H,t), 2.17 (6H,s), 2.63 (3H,s), 3.78 (3H,s), 6.10 (1H,s), 6.7–7.2 (4H,m,aryl).

$^{13}$C NMR: (CDCl$_3$)δ14.92(q), 18.11(t), 36.32(t), 40.16(t), 43.03(q), 43.47(s), 45.80(q), 46.28(t), 55.11(q), 60.80(t), 109.02(s), 110.32(d), 114.33(d), 120.68(d), 128.52(d), 136.64(d), 151.65(s), 159.24(s).

PREPARATION OF 4β-(3-METHOXYPHENYL)-1,3α-DIMETHYL-4α-PROPYLPIPERIDINE

A suitable hydrogenation vessel was charged with 5 g of 5% palladium on calcium carbonate followed by a solution of 10 g (0.033 mol) of 1,4,5,6-tetrahydro-4-(3-methoxyphenyl)-N,N,1-trimethyl-4-propyl-3-pyridinemethanamine in 200 ml of triethylamine. The vessel was placed in a hydrogenation apparatus under a hydrogen pressure of 60 psi and agitated for approximately 16 hours at which point hydrogen uptake had ceased. The catalyst was removed by filtration through infusorial earth and the solvent of the filtrate was removed by evaporation under reduced pressure. The residue contained 8.08 g of an oil chromatographically analyzed as containing 67.2% 4β-(3-methoxyphenyl)-1,3α-dimethyl-4α-propylpiperidine and 30.8% 4β-(3-methoxyphenyl)-1,3β-dimethyl-4α-propylpiperidine. The material thus obtained was used directly in the following demethylation step.

PREPARATION OF (±)-3-(1,3-DIMETHYL-4-PROPYL-4-PIPERIDINYL)PHENOL

Five grams (0.019 mol) of the crude mixture of 4β-(3-methoxyphenyl)-1,3α-dimethyl-4α-propylpiperidine and 4β-(3-methoxyphenyl)-1,3β-dimethyl-4α-propylpiperidine as obtained above was dissolved in 12.5 ml of 48% aqueous hydrobromic acid and the solution was heated at reflux for 6 hours. The mixture was cooled and neutralized to pH 8 with concentrated ammonium hydroxide. The resulting suspension was extracted with two 10 ml portions of ethyl acetate. The organic layers were combined and washed with two 10 ml portions of water, once with 5 ml of a saturated sodium chloride solution and dried over anhydrous sodium sulfate. Evaporation of the volatiles under reduced pressure provided 3.6 g of (±)-3-(1,3α-dimethyl-4α-propyl-4β-piperidinyl)phenol contaminated with the diastereomeric β-isomer (α/β=7/3 by chromatographic analysis). Yield 77%.

PREPARATION OF (±)-3-(1,3α-DIMETHYL-4α-PROPYL-4β-PIPERIDINYL)PHENOL, HYDROCHLORIDE (PICENADOL)

The crude 3.6 g (0.0146 mol) of (±)-3-(1,3α-dimethyl-4α-propyl-4β-piperidinyl)phenol was dissolved in 15 ml of 1N hydrochloric acid with heating to approximately 80° C. The solution was filtered hot and allowed to gradually cool whereupon 2.3 g of crystalline (±)-3-(1,3α-dimethyl-4α-propyl-4β-piperidinyl)phenol, hydrochloride dihydrate was collected by filtration. The yield was 70% based on the amount of α-isomer present in the initial mixture.

A 35 g portion of (±)-3-(1,3α-dimethyl-4α-propyl-4β-piperidinyl)phenol, hydrochloride dihydrate was dissolved in 135 ml of absolute ethanol with heating and the material was allowed to crystallize slowly upon cooling. The crystals were filtered and washed with approximately 50 ml of ethanol and dried to provide 27.2 g of purified (±)-3-(1,3α-dimethyl-4α-propyl-4β-piperidinyl)phenol, hydrochloride (picenadol). Yield 87.5%. The picenadol thus prepared was identical to that of Zimmerman in U.S. Pat. No. 4,081,450 by NMR.

I claim:

1. A process for preparing a 1,4-dialkyl-3-methyl-4-(3-substituted phenyl)piperidine of the formula

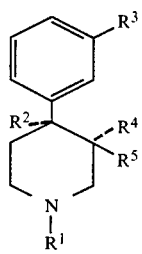

wherein $R^1$ and $R^2$ are independently $C_1$–$C_4$ alkyl, $R^3$ is $C_1$–$C_3$ alkoxy, and one of $R^4$ and $R^5$ is methyl and the other is hydrogen, comprising reacting a 1,4-dialkyl-4-(3-substituted phenyl)tetrahydropyridine of the formula

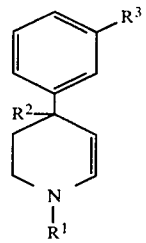

with formaldehyde and $NHR^6R^7$, wherein $R^6$ and $R^7$ are independently $C_1$–$C_3$ alkyl or, when taken together with the nitrogen atom to which they are attached, form piperidine, piperazine, N-methylpiperazine, morpholine or pyrrolidine, at a pH from about 1.0 to about 5.0, and in the presence of an acid which provides a non-nucleophilic anion, to prepare a 1,4-dialkyl-4-(3-substituted phenyl)-3-tetrahydropyridinemethanamine of the formula

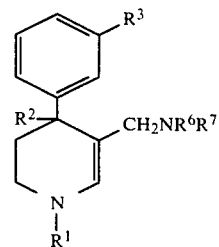

and reducing that product by hydrogenation over a palladium catalyst in a basic reaction medium.

2. A process of claim 1 wherein $R^1$ is methyl.
3. A process of claim 2 wherein $R^2$ is n-propyl.
4. A process of claim 3 wherein $R^3$ is methoxy.
5. A process of claim 4 wherein both $R^6$ and $R^7$ are methyl.
6. A process of claim 5 wherein the acid is sulfuric acid.
7. A process of claim 6 wherein the catalyst is a palladium on carbon catalyst.

* * * * *